US008082172B2

(12) United States Patent
Chao et al.

(10) Patent No.: US 8,082,172 B2
(45) Date of Patent: Dec. 20, 2011

(54) SYSTEM AND METHOD FOR PEER-PROFILING INDIVIDUAL PERFORMANCE

(75) Inventors: David Yung-Min Chao, Austin, TX (US); William Wyeleem Chan, Austin, TX (US); Mike Vineet Kadyan, Austin, TX (US)

(73) Assignee: The Advisory Board Company, Washington, DC (US)

( * ) Notice: Subject to any disclaimer, the term of this patent is extended or adjusted under 35 U.S.C. 154(b) by 1305 days.

(21) Appl. No.: 11/408,560

(22) Filed: Apr. 21, 2006

(65) Prior Publication Data

US 2006/0241974 A1   Oct. 26, 2006

Related U.S. Application Data

(60) Provisional application No. 60/675,382, filed on Apr. 26, 2005.

(51) Int. Cl.
G06Q 10/00 (2006.01)
(52) U.S. Cl. ............................ 705/7.39; 705/2; 705/7.42
(58) Field of Classification Search ............. 705/2, 7.39, 705/7.42
See application file for complete search history.

(56) References Cited

U.S. PATENT DOCUMENTS

| 5,652,842 | A* | 7/1997 | Siegrist et al. ............... 705/2 |
| 6,877,034 | B1* | 4/2005 | Machin et al. ............... 709/223 |
| 2003/0004789 | A1* | 1/2003 | Calderaro et al. ............. 705/11 |
| 2003/0163352 | A1* | 8/2003 | Surpin et al. ................. 705/2 |
| 2006/0161456 | A1* | 7/2006 | Baker et al. .................. 705/2 |

OTHER PUBLICATIONS

Crimson Services, Solutions for Physician Performance Management, Retrieved from web.archive.org on Feb. 2, 2010, from Aug. 25, 2004 posting.*
Micklitsch, Christine and Ryan-Mitlyng, Theresa. Physician Performance Management: Tool for Survival and Success. Medical Group Management Association, 1996. pp. 23-24.*
S. Juncosa, B. Bolibar, M. Roset, and R. Tomas. Performance of an Ambulatory Casemix measurement system in primary care in Spain. European Journal of Public Health, 1999, 9: 27-35.*
Chilingerian, Jon A. Evaluating physician efficiency in hospitals: A multivariate analysis of best practices. European Journal of Operations Research 80 (1995) 548-574.*
Texas Health Care Information Council User Manual for Texas Hospital Inpatient Discharge Public Use Data File 2003, pp. 1-54, 2003.
E. Andrew Balas, et al. "*An Expert System for Performance-based Direct Delivery of Published Clinical Evidence*," research papers, Journal of the American Medical Informatics Association, vol. 3, No. 1, pp. 56-65, Jan. 1996.
R. Averill, et al. "*What Are APR-DRGS? An Introduction to severity of Illness and Risk of Mortality Adjustment Methodology*," 3M Health Information Systems, Salt Lake City, UT, pp. 1-4, 2003.

\* cited by examiner

*Primary Examiner* — Beth V Boswell
*Assistant Examiner* — Stephanie Zagarella
(74) *Attorney, Agent, or Firm* — Sprinkle IP Law Group

(57) ABSTRACT

Embodiments of the invention provide a comprehensive, automated system and method for evaluating the performance of individuals or entities employed by an organization, particularly useful in peer-profiling physician performance in multi-facility environments. Embodiments of the invention can dynamically compose a virtual peer or group of peers and perform peer-profiling on each individual or group of individuals to be evaluated. For example, a composite physician may be generated from system-wide and/or state-wide healthcare data as a benchmark against which a particular physician is profiled according to industry-standard measurements. The composite physician would have equivalent or similar job function(s) as well as patient population. The composite physician enables a comprehensive "apple to apple" comparison with the particular physician, giving meaning to and facilitating the usefulness of performance evaluation results.

17 Claims, 12 Drawing Sheets

SYSTEM AND METHOD FOR PEER-PROFILING INDIVIDUAL PERFORMANCE

CROSS-REFERENCE TO RELATED APPLICATIONS

This application claims priority from U.S. Provisional Patent Application Ser. No. 60/675,382, filed Apr. 26, 2005, and entitled "SYSTEM AND METHOD FOR IDENTIFYING, EVALUATING AND MONITORING PHYSICIAN PERFORMANCE IN MULTI-FACILITY ENVIRONMENTS," which is hereby incorporated herein by reference in its entirety for all purposes.

FIELD OF THE INVENTION

This invention relates generally to job performance analysis. More particularly, this invention relates to evaluating the performance of an individual or other entity overseen or employed by an organization. Embodiments of the invention disclosed herein can be particularly useful in peer-profiling physician performance in multi-facility environments.

BACKGROUND OF THE INVENTION

Despite technological advances in recent years, evaluating an individual's job performance or productivity in a fair, objective, and comprehensive manner remains a difficult task. Complexity of a job function can also complicate the task of performance evaluation. What is more, if a job function or specialty is somewhat rare or unique, it can be difficult to set a performance standard or find a comparable peer for the individual. As an example, healthcare professionals such as physicians and, nurse practitioners typically have distinctive specialties and often perform complex job functions. Thus, it can be difficult to comprehend and gauge the performance levels of these healthcare professionals. In current healthcare systems (e.g., hospitals, hospital systems, integrated delivery networks, etc.), administrators generally have a good understanding of the overall, collective performance at the organization level. However, they do not evaluate the performance of individual healthcare professionals because existing computerized healthcare systems are not designed to track the performance levels of individual healthcare professionals. Consequently, administrators lack viable technological tools to help identify healthcare professionals with inadequate performance levels and initiate remedial processes to improve the performance levels.

For example, in some cases, administrators might be able to spot 'problem physicians' based on a limited subset of data or measures. Often times, identification is based on word-of-mouth. The problem with these approaches is that the results tend to be anecdotal and underestimate the true population of physicians that require performance improvement guidance. As discussed above, computerized healthcare systems in place today typically monitor performance at the aggregate (i.e., at the organizational level). Human investigation and research are generally required to identify potential 'problem physicians' or the like. The investigation and research process can be tedious and time consuming. Furthermore, manual investigation often does not cover the full spectrum of a physician's job function. As a result, the information gathered may not be accurate or conducive to allowing an administrator to make a fair and comprehensive determination about the overall performance level of the physician. More importantly, in current approaches, the performance of a physician or a group of physicians is typically not evaluated against peers who perform equivalent or similar job functions and/or specialties and who have equivalent or similar patient populations. Because existing performance evaluation processes generally lack peer comparison, physicians tend to dispute performance evaluation results and/or mitigate with an excuse that they had been compared with physicians with different specialties and/or different patient populations.

Another obstacle in evaluating the performance levels of healthcare professionals is the sheer number of hundreds to thousands of healthcare professionals caring for hundreds and thousands of patients for various illnesses on a daily basis within each healthcare system, which can comprise multiple facilities. Given the typical high diversity of cases taken by health care professionals, especially physicians, it can be overwhelmingly time consuming and tedious to evaluate and analyze each individual's performance level in every observable category even within a reasonable time period (e.g., a quarter, 6-month, one year, or two years). While administrators might be able to identify a few individuals with clearly inadequate performance levels within a facility, they are not equipped to timely identify and manage potentially hundreds to thousands of healthcare professionals who are not performing at the generally accepted or specified performance levels. The inability to timely identify healthcare professionals with inadequate performance levels can lead to potential problems in the overall quality of the medicine practiced in these facilities, which in turn may reduce the overall productivity and profitability of the healthcare system.

A need exists for a comprehensive, automated system and method for accurately peer profiling the performance of an individual or other entity employed by an organization. Embodiments of the present invention can address this need and more.

SUMMARY OF THE INVENTION

Embodiments of the present invention provide a comprehensive, automated system and method for evaluating the performance of individuals or entities overseen or employed by an organization. Embodiments of the invention disclosed herein can be particularly useful in peer-profiling physician performance in multi-facility environments.

Embodiments of the present invention can address the problems described above with respect to healthcare professionals by integrating several unique approaches:
  Consider industry-standard measurements relevant to an individual's performance in a comprehensive manner.
  Fine tune individual performance levels according to a variety of factors. For example, a physician's performance can be adjusted according to the diagnoses of his/her cases, as well as the severity (i.e., level of sickness and/or mortality) of each patient so that the physician's performance can be accurately compared to similar physicians (i.e., his/her peers).
  Compose a virtual peer or group of peers and perform peer-profiling on each individual or group of individuals to be evaluated. Such a virtual peer or group of peers can be compiled from data aggregated and processed at a central location. For example, a composite physician may be generated from system-wide and/or state-wide healthcare data as a benchmark against which a particular physician is profiled. The composite physician would have equivalent or similar job function(s) as well as patient population. In other words, the composite physician would enable an "apple to apple" comparison with the particular physician, giving meaning to and facilitating the usefulness of performance evaluation results.

Calculate and present performance evaluation results (e.g., percentile rankings and scores, etc.) in a centralized, readily accessible fashion and in a unified format that can be easily understood by administrators. For example, present the performance evaluation results via a Web based application can facilitate the administrators to take appropriate action in a timely manner.

Embodiments of the invention can save healthcare administrators and hence healthcare systems significant time and resources and reduce risks as well as costs related to managing healthcare professionals. More specifically, in one embodiment, a physician's disparate performance data is distilled into a single number and compared to a similarly distilled single number based on the physician's peer performance. Embodiments of the invention can facilitate healthcare administrators and analysts alike to identify 'problem physicians' and take appropriate action in a timely manner, eliminating the need for tedious and time consuming manual investigation and research. Embodiments of the invention enable healthcare administrators to track the performance of individual healthcare professionals and to quickly identify the most critical set of physicians that require changes in their performance. The identification is also accurate and reliable because it is based on actual, comprehensive data and not word of mouth.

Other objects and advantages of the present invention will become apparent to one skilled in the art upon reading and understanding the detailed description of the preferred embodiments described herein with reference to the following drawings.

DETAILED DESCRIPTION

The invention and various features and advantageous details thereof are explained more fully with reference to the exemplary, and therefore non-limiting, embodiments illustrated in the accompanying drawings and detailed in the following description. Descriptions of known programming techniques, computer software, hardware, operating platforms and protocols may be omitted so as not to unnecessarily obscure the invention in detail. It should be understood, however, that the detailed description and the specific examples, while indicating the preferred embodiments of the invention, are given by way of illustration only and not by way of limitation. Various substitutions, modifications, additions and/or rearrangements within the spirit and/or scope of the underlying inventive concept will become apparent to those skilled in the art from this disclosure.

Figure 1:
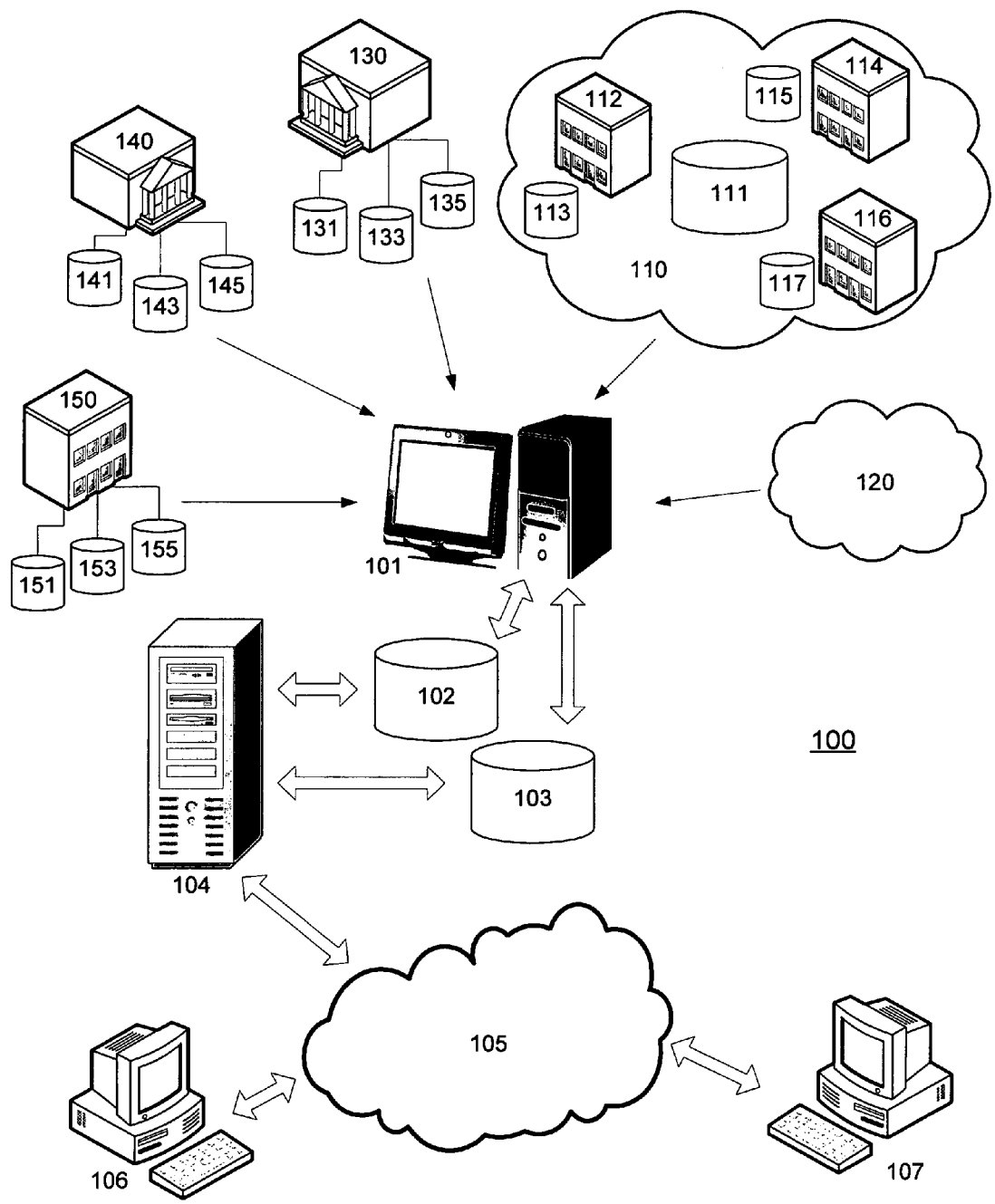
FIG. 1 is a diagrammatic representation of exemplary hardware architecture in which embodiments of the present invention may be implemented.

FIG. 1 is a diagrammatic architectural representation of computing environment 100 in which embodiments of the present invention may be implemented. In this example, computing environment 100 comprises a computer system 101, one or more data repositories 102, 103, server 104, communications means 105, and one or more clients 106, 107. According to one aspect of the invention, computing environment 100 is operable to evaluate the performance of an individual or entity employed by an organization. In FIG. 1, such an organization is represented by reference numbers 110, 120, 130, 140, 150. An organization could be a company or corporation comprising multiple groups or facilities. In this example, organization 110 has a plurality of facilities 112, 114, 116. These facilities may or may not be independently operated and/or owned. Each organization may have one or more databases and each facility may have its own database(s). In addition, an organization may have a global database. Following the example of organization 110, database 113 is configured for facility 112, database 115 is configured for facility 114, database 117 is configured for facility 116, and database 111 is configured for organization 110. Organization 120 may be a multi-facility company like organization 110. Organization 130 may be a government agency having databases 131, 133, 135. Organization 140 may be another government agency having databases 141, 143, 145. Organization 150 may be an independent agency having databases 151, 153, 155. These organizations (e.g., 110, 120, 130, 140, 150) may have access to communications means 105 through client computers (e.g., 106, 107).

In the example shown in FIG. 1, computer system 101 is operable to collect data from various disparate sources (e.g., 110, 120, 130, 140, 150), calculate measures or statistics from the data collected, and store the calculated information in one or more data repositories or data warehouses (e.g., 102, 103). A data warehouse is a repository storing integrated information for efficient querying and analysis. Data warehousing infrastructure and techniques are known in the art and thus not further described herein. Server 104 is representative of servers (e.g., application server(s), Web server(s), email server(s), etc.) that are operable to communicate with computer system 101 and data warehouses 102, 103 as well as distributed clients 106, 107 through communications 105 in computing environment 100. Computer executable instructions implementing embodiments of the invention may be stored in a computer readable medium residing or communicatively coupled to computer system 101, data warehouses 102, 103, server 104, clients 106, 107, or a combination thereof. In one embodiment, communications means 105 comprises the Internet.

Embodiments of the invention disclosed herein can be particularly useful in peer-profiling physician performance in multi-facility environments. In one embodiment, organization 110 can be a hospital system and facilities 112, 114, 116 can be individual hospitals within hospital system 110. In one embodiment, organization 130 can be a state-level agency (e.g., the Texas Health Care Information Council (THCIC)). In one embodiment, databases 131, 133, 135 can comprise Public Use Data collected by state agency 130. In one embodiment, organization 140 can be a national-level agency (e.g., Agency for Healthcare Research and Quality (AHRQ)). In one embodiment, databases 141, 143, 145 can comprise Healthcare Cost and Utilization Project (HCUP) data collected by national agency 140.

Figure 2:
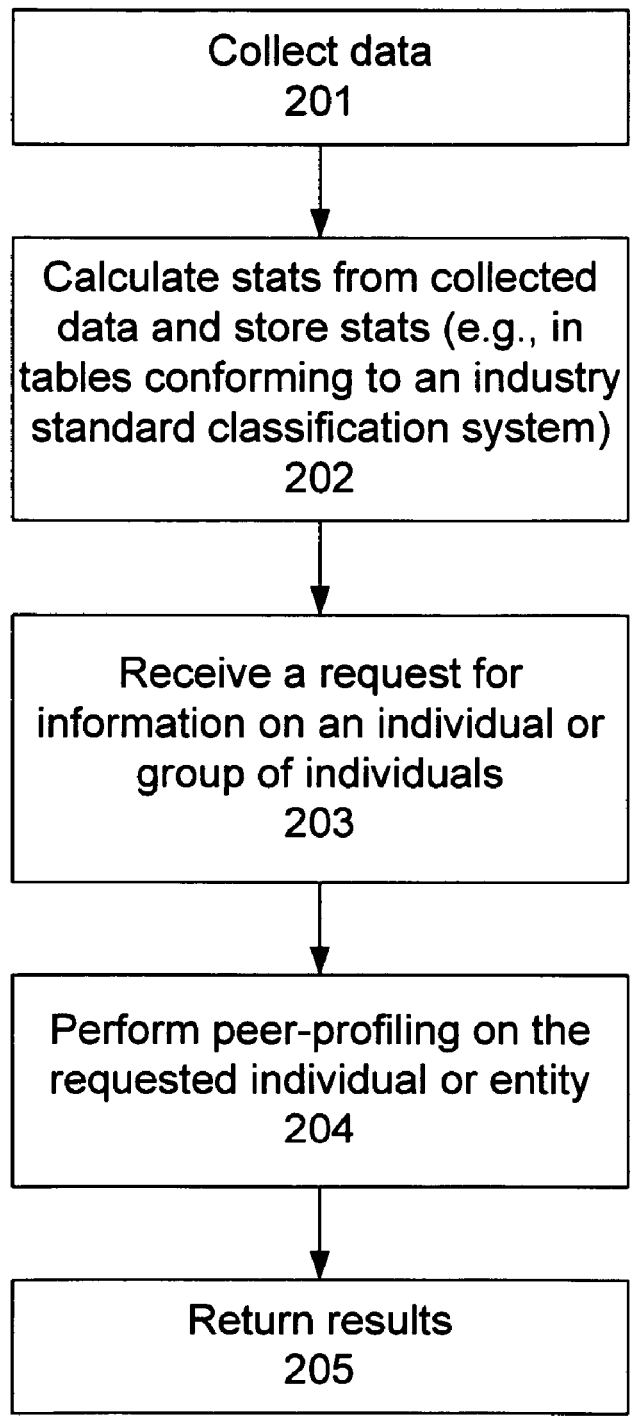
FIG. 2 is a flow diagram illustrating an exemplary process implementing embodiments of the present invention.

FIG. 2 is a flow diagram illustrating an exemplary process 200 implementing embodiments of the present invention. According to embodiments of the invention, data can be collected from disparate sources (e.g., organizations 110, 120, 130, 140, and/or 150) at step 201. In one embodiment, at step 201, data from hospital system 110, state agency 130, national agency 140, and perhaps international or independent agency 150 can be aggregated at computer system 101. An exemplary independent agency 150 may be a standards-setting body and/or accrediting body such as the Joint Commission on Accreditation of Healthcare Organizations (JCAHO) from Illinois, USA. As one skilled in the art can appreciate, data can be loaded into computer system 101 in various ways through computer-readable media (e.g., compact disc read-only memory (CD ROM) discs, data storage media, floppy disks, flash memory devices, etc.) and/or Web-downloadable electronic files, etc.

At step 202, statistical analyses can be performed (e.g., at computer system 101) on the collected data. The results are correspondingly stored (e.g., as tables in database 102) in a format which may conform to a standard data classification system. In one embodiment, computer system 101 is operable to calculate physician stats or performance measures from data collected at step 201 and store the physician stats in database 102. Database 102 can be a dedicated data warehouse for hospital system 110. In one embodiments the 3M™ APR™ DRG (All Patient Refined Diagnosis Related Groups) Classification System, or APR-DRG for short, is utilized in defining criteria used in structuring database 102. APR-DRG is a standard patient classification system that relates the types of patients treated to the resources they consumed. Hospitals generally utilize APR-DRG to classify patients and determine payment rates. APR-DRG is known in the art and thus not further described herein. Other healthcare related classification systems exist and may be utilized to implement embodiments of the invention. For example, disease staging classification systems, All Patient DRG (AP-DRG) Classification System, All Patient Severity DRG (APS-DRG)) Classification System, and so on may be utilized to define data elements and/or criteria forming the structure of database 102. As one skilled in the art will appreciate, depending upon implementations, different classification systems may be utilized. Therefore, classification systems described herein are meant to be exemplary and not limiting embodiments of the invention.

Figure 5:
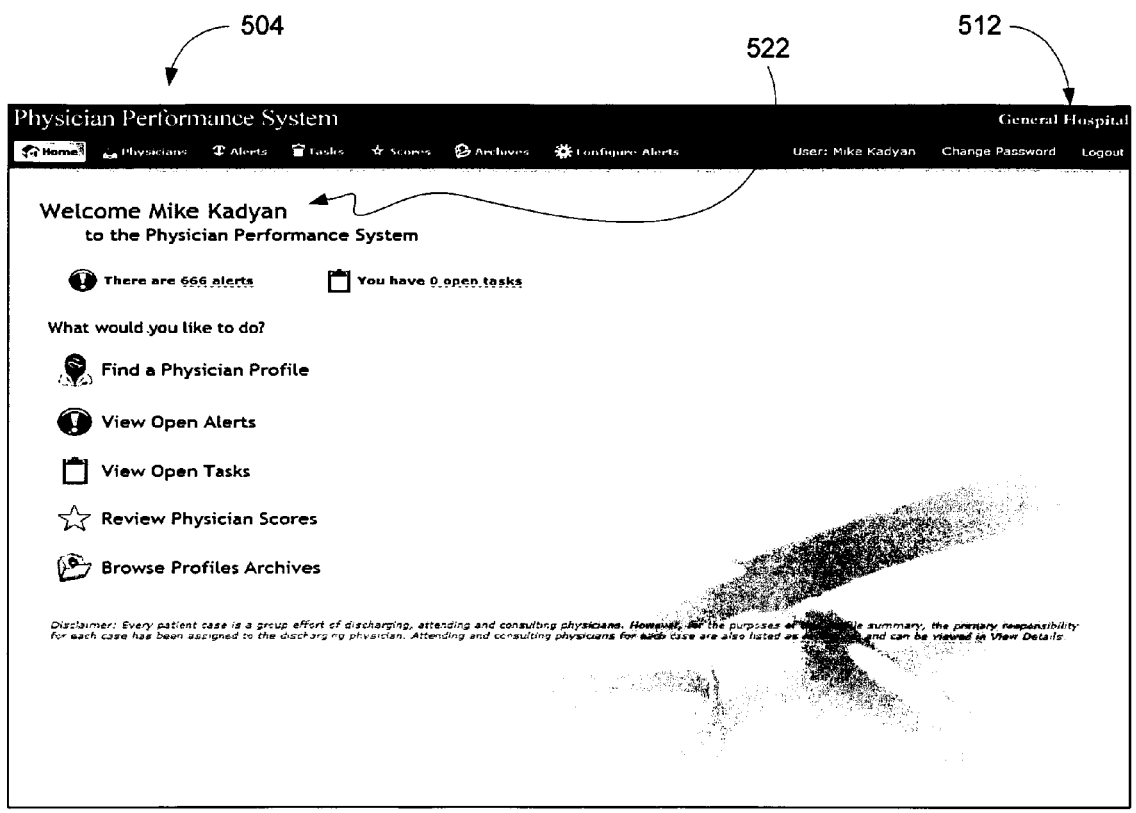
FIG. 5 is a screenshot of a user interface implementing one embodiment of the invention.
Figure 6:
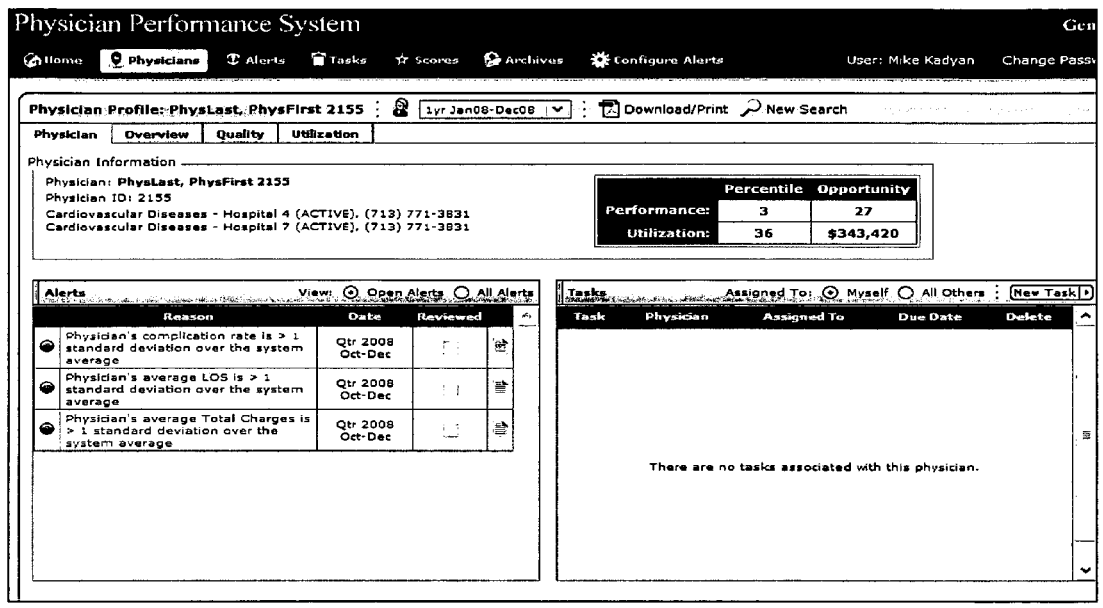
FIGS. 6-12 are screenshots representative of a comprehensive physician profile, exemplifying embodiments of the invention.

At step 203, a user request may be received (e.g., at server 104) inquiring information on an individual (e.g., a physician) employed by an organization (e.g., hospital system 110). The requested information may relate to the individual's performance within a period of time (e.g., quarter, year, two years, etc.). In one embodiment, at step 203, a request is received (e.g., at server 104) for information on a physician (e.g., "PhysFirst 2155 PhysLast"). The request may be from an authorized user (e.g., at client 106) of hospital system 110. In this example, users may include medical directors, physicians, chief operating officers, department heads, service line chiefs, etc. FIG. 5 shows screenshot 500 that illustrates one embodiment of the invention. General Hospital 512 of FIG. 5 may be a facility of hospital system 110 illustrated in FIG. 1. In the example shown in FIG. 5, user 522 is authorized to access an embodiment of the invention named Physician Performance System 504 through a Web-based application with appropriate user ID and password. In this case, user 522 wishes to find a physician profile on a physician named "PhysFirst 2155 PhysLast".

At step 204, the requested performance information can be automatically calculated based on data stored in a central data repository implementing embodiments of the invention (e.g., database 102). According to embodiments disclosed herein, at step 204, a virtual peer of the individual is automatically and dynamically composed so as to facilitate the user who requested the information to accurately evaluate the individual's performance. According to embodiments disclosed herein, the virtual peer is composed in a manner so that its profile would match or substantially match the individual's profile. In some cases, there may be a plurality of evaluation categories or measures and a virtual peer might be composed for each measure. In this way, the virtual peer's performance can serve as a benchmark to the individual's performance in each evaluation category or measure, thus allowing for an "apple to apple" comparison in each relevant category and providing a meaningful overall profile on the individual's performance. Embodiments implementing a peer-profiling system and method will be described below in more details with reference to FIGS. 3 and 4. In one embodiment, the individual being evaluated and/or profiled is a physician and his/her virtual peer is a composite physician whose profile is compiled from actual data of other physicians. An exemplary user interface implementing one embodiment of the peer-profiling system is shown in FIG. 5. FIGS. 6-12 are screenshots showing an exemplary profile implementing embodiments of the peer-profiling system and method disclosed herein. As an example, at step 204, server 104 can be configured to, in response to the user request, dynamically and automatically compose a virtual peer of PhysFirst 2155 PhysLast, compare PhysFirst 2155 PhysLast's performance against his/her virtual peer (e.g., "System"), and correspondingly generate a Physician Profile on PhysFirst 2155 PhysLast.

At step 205, the requested performance information is returned (e.g., as Hypertext Markup Language (HTML) documents or Web pages) and presented to the user (e.g., via a user interface). One embodiment resides at an application server and communicates the results to a Web server which, in turn, communicates the results to a client machine (e.g., client 106) through appropriate communications means (e.g., Internet 105). Client 106 can be configured to present the results to the user via Web-based application. As described above, in the example shown in FIG. 1, server 104 is representative of server machine(s) (e.g., application server, Web server, etc.) programmed to function in client-server computing environment 100 for implementing embodiments of the invention. Client-server architecture and computer network communications protocols are known in the art and thus are not further described herein. Following the above example, the Physician Profile of PhysFirst 2155 PhysLast can be returned to the requesting user at step 205. In one embodiment, the Physician Profile may be communicated to a Web server at server 104. Web server may operate to encode the Physician Profile into Web compatible format(s) (e.g., as HTML documents) before serving the Physician Profile to the requesting user's Web browser (e.g., at client 106). In one embodiment, database 102 may be structured to store integrated information for efficient querying and analysis by server 104, thus enabling the request-response time between client 106 and server 104 to be very fast and near real time.

Figure 3:
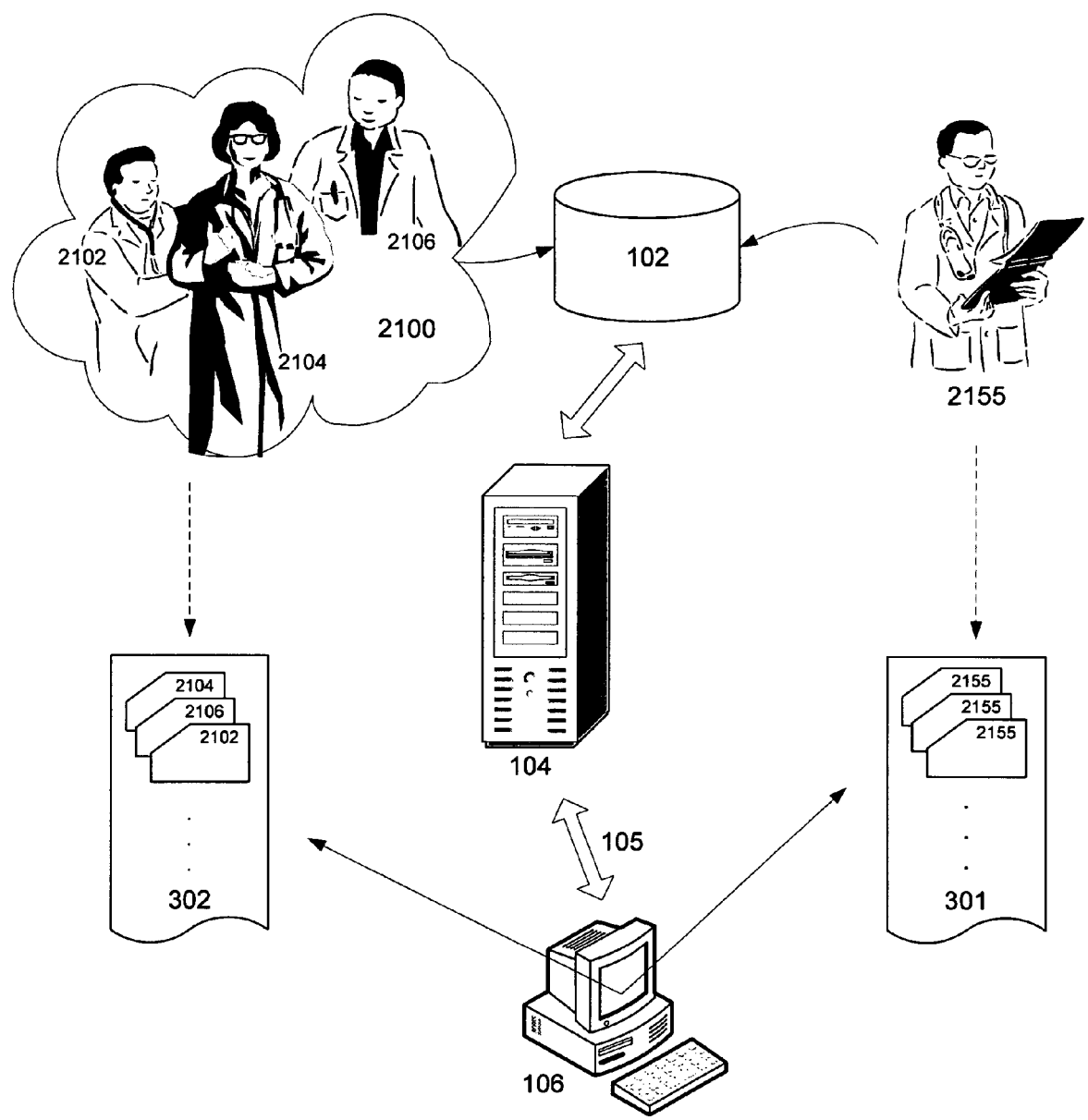
FIG. 3 is a diagrammatic representation of an exemplary system implementing a peer-profiling methodology according to embodiments of the present invention.

FIG. 3 is a diagrammatic representation of an exemplary system 304 implementing a peer-profiling methodology according to embodiments of the present invention. In the example shown in FIG. 3, system 304 comprises server 104 communicatively coupled to database 102 and client 106 over suitable communications means (e.g., network communications link 105) as described above with reference to FIG. 1. As describe above, in one embodiment, database 102 can be a dedicated data warehouse storing information related to physicians working in a hospital or hospital system (e.g., hospital system 110). In this example, in response to a request from client 106 over network communications link 105, server 104 operates to retrieve information related to PhysFirst 2155 PhysLast from database 102. Based on the retrieved information (e.g., criteria related to the specialty and patient population of PhysFirst 2155 PhysLast), server 104 determines and retrieves relevant data needed to compute a composite physician 2100. As exemplified in FIG. 3, composite physician 2100 may be derived from an actual physician or a composite of two or more physicians (e.g., physicians 2102, 2104, 2106). In the example shown in FIG. 3, physician profile 301 based on performance information of PhysFirst 2155 PhysLast is returned and represented to a user at client 106 along with composite physician 2100's benchmark information 302, which is composed of actual data from cases handled by other physicians (e.g., physicians 2102, 2104, 2106). According to one embodiment of the invention, composite physician 2100 is equivalent or substantially similar to PhysFirst 2155 PhysLast so that they can be compared "apples to apples" in every observable measure (e.g., mortality rate).

In one embodiment, system 304 can calculate and present individual statistics of interest for each physician for a period of time (e.g., a quarter, year, or two-year period). The calculated results may be presented to a user through a Web-based user interface. An example of such a user interface is shown in FIG. 5, implementing Physician Performance System 504. In one embodiment, system 304 can calculate statistics to measure performance with respect to each of the discharges handled by a physician over a specified period. For example, system 304 can operate to calculate the average charge and average mortality rate of PhysFirst 2155 PhysLast over a two year period.

Beyond presenting individual results, system 304 can facilitate interpretation of a physician's statistics in at least two ways:

Providing a breakdown for several of the calculated quantities on the level of results for different measures (e.g., APR-DRG codes, severity levels, and/or risk of mortality levels). As one skilled in the art can appreciate, a mortality level rate that seems 'high' for discharges with one particular APR-DRG value may seem relatively 'low' for another. Thus, the breakdown or segmentation in representation can facilitate a user to make better "apples to apples" comparisons in each measure or category of performance. In one embodiment, calculated performance statistics can be separately represented in each measure or category of discharges according to APR-DRG classification. Other classifications may be utilized in various implementations.

Providing average results garnered from the physician's (actual and virtual) peers. As describe above, to evaluate a physician's performance in a comprehensive, fair, and meaningful way, the physician's performance statistics should be compared with those of his/her peers (i.e., other doctors within the same hospital system and/or from across the state), much like comparing "Fuji apples to Fuji apples". In embodiments of the invention, such a comparison can have various levels of sophistication. For example, one embodiment of the invention can sub-segment cases that are classified as having the same disease or illness but different severities (i.e., patients who had pneumonia and were at high risk of death versus patients who had mild pneumonia). As another example, one embodiment of the invention can compare a physician (e.g., PhysFirst 2155 PhysLast of FIG. 3) with a virtual peer (e.g., composite physician 2100, which is a composite of two or more actual physicians 2102, 2104, 2106) by mortality rate in each of the different APR-DRG classes of discharges over a specified period with average results from physicians 2102, 2104, 2106 in their respective cases which correspondingly match the same APR-DRG classes of discharges.

In one embodiment, PhysFirst 2155 PhysLast's disparate results are distilled into a single number, which is then compared to a similarly distilled single number based on composite physician 2100's performance. In this embodiment, system 304 is operable to take relevant data (e.g., mortality rate, etc.) from other physicians (e.g., physicians 2102, 2104, 2106) across all different types of discharges and generate a number comparable to that of PhysFirst 2155 PhysLast. More specifically, PhysFirst 2155 PhysLast's overall score on mortality rate is first calculated by dividing the total number of discharges by PhysFirst 2155 PhysLast involving mortalities in a period of one year by the total number of discharges by PhysFirst 2155 PhysLast (i.e., regardless of mortality) within the same year. Next, composite physician 2100's mortality rate is calculated by dividing up all discharges (e.g., from organizations 110, 112, 114, 116, 130, 140, and/or 150) into distinct sets of discharges according to a set of criteria. In one embodiment, the set of criteria is defined according to the 3M Risk of Mortality Level and APR-DRG. In this embodiment, system 304 is operable to calculate, for each set of discharges with a common APR-DRG code and Risk of Mortality level, the average mortality for PhysFirst 2155 PhysLast's peer (i.e., composite physician 2100) by dividing the number of discharges with mortality in that set by the total number of discharges regardless of mortality in the same set.

After determining average mortality rates for the requested physician (e.g., PhysFirst 2155 PhysLast) and his peer (e.g., composite physician 2100), system 304 is operable to determine the distribution of the physician's cases with regard to a specified combination of standardized classes/measures over the same period of time and form a comparison with his peer by configuring the peer's cases over the same distribution ratio. As an example, assuming that 30% of all PhysFirst 2155 PhysLast's cases can be categorized in APR-DRG (89) Simple Pneumonia at the Extreme Risk of Mortality Level, and 70% of all PhysFirst 2155 PhysLast's cases can be categorized in APR-DRG (141) Asthma at the Moderate Risk of Mortality Level. To form a comparison, the average mortality rates for the requested physician's peer can be correspondingly adjusted according to the same distribution. In this example, composite physician 2100's adjusted mortality rate average=30%*(APR-DRG=Simple Pneumonia, Risk of Mortality=Extreme)+70%*(APR-DRG=Asthma, Risk of Mortality=Moderate).

In this manner, if a doctor meets the average mortality rate in each class of discharges, his/her mortality rate would match his/her peer average mortality rate over the same period. If his/her mortality rates are higher in both classes, then his/her mortality rate average would be greater than his/her peer's mortality rate average, possibly signaling a performance issue as compared to his peers.

In some cases, PhysFirst 2155 PhysLast could be the only physician in system 304 who has handled a rare illness and thus the only statistic relevant to that rare illness in database 102 would be PhysFirst 2155 PhysLast's own data. In those rare instances, PhysFirst 2155 PhysLast could be his/her own peer.

The above example illustrates one embodiment of the invention. In other embodiments, a physician may cover hundreds of distinct APR-DRG, Mortality Risk Level combinations over a period of time. In these cases, a computer system according to embodiments of the invention can be programmed to determine a physician's average mortality rate as described above and obtain a single 'peer average' figure for comparison, weighting peer averages in each class in proportion to the percentage of cases that the individual physician actually handled over the period. The same approach describe above can be generalized beyond the simplified example of mortality rate. For example, the computer system can be programmed to calculate a physician's average Length of Stay for discharges and compare it to a 'peer average' Length of Stay based on peer averages in each class of discharges as well as the physician's actual proportion of cases in each class.

As one skilled in the art can appreciate, embodiments of the invention can be implemented in various ways. For example, "PhysFirst 2155 PhysLast" can be representative of any individual (e.g., a healthcare professional, a nurse practitioner, a doctor, a physical therapist, a lawyer, a litigator, a manager, etc.) or entity (e.g., a group of students, a group of doctors, etc.) whose performance is peer-profiled according to embodiments of the invention. In the latter case, the average or median of the group can be calculated and then compared with the group's peer average as describe above.

According to embodiments of the invention, peer average calculations can be adjusted based on a set of filtering criteria to enhance the peer-profiled performance evaluation for each measure. Adjusted peer averages can provide the closest and most accurate representation of a peer comparison for a physician per measure. In one embodiment, adjustments (i.e., filtering criteria) can be APR-DRG and Severity levels specified for a specific measure. Other adjustments are possible and can be one or more of the following:

APR-DRG (case mix) adjustment—a set of cases with identical APR-DRGs as the physician is used to calculate the peer average.

Severity adjustment—a set of cases with identical severity levels as the physician is used to calculate the peer average. In one embodiment, this adjustment is used as a secondary adjustment, in conjunction with an APR-DRG adjustment.

Mortality adjustment—a set of cases with identical mortality risks as the physician is used to calculate the peer average. In one embodiment, this adjustment is used as a secondary adjustment, in conjunction with an APR-DRG adjustment.

Hospital adjustment—a set of cases at the same or similar hospital or hospital type (e.g., an academic hospital or a hospital-like setting) as the physician is used to calculate the peer average. In one embodiment, this adjustment is used as a tertiary adjustment, in conjunction with an APR-DRG and severity adjustments.

Additional exemplary adjustments can be found in the Appendix A, "Crimson Physician Performance System Help Text", submitted concurrently with this disclosure.

To illustrate, Table 1 below provides two sets of sample data, where the first set contains patient case data for Cardiologist A and the second data set reflects case data for the entire hospital system.

TABLE 1

| Patient Data for Cardiologist A's Cases | | | | | Patient Data for System-wide Cases | | | |
| --- | --- | --- | --- | --- | --- | --- | --- | --- |
| Case # | Patient Name | Patient Age | APR-DRG | Severity | Case # | Specialty | APR-DRG | Severity |
| 1 | Patient1 | 79 | 180 | 1 | 1 | Cardiology | 180 | 1 ✓ |
| 2 | Patient2 | 65 | 120 | 2 | 2 | Cardiology | 120 | 2 ✓ |
| 3 | Patient3 | 72 | 180 | 1 | 3 | Pulmonary | 140 | 3 |
| 4 | Patient4 | 95 | 115 | 2 | 4 | Radiology | 180 | 3 |
| 5 | Patient5 | 58 | 120 | 1 | 5 | Cardiology | 160 | 1 |
| | | | | | 6 | Cardiology | 115 | 4 |
| | | | | | 7 | Internal | 120 | 2 ✓ |
| | | | | | 8 | Pulmonary | 130 | 2 |
| | | | | | 9 | Cardiology | 115 | 2 ✓ |
| | | | | | 10 | Pulmonary | 120 | 1 ✓ |
| | | | | | 11 | Cardiology | 120 | 3 |
| | | | | | 12 | Pulmonary | 150 | 3 |
| | | | | | . | | | |
| | | | | | . | | | |
| | | | | | n | Pulmonary | 140 | 4 |

In this example, an adjustment or filtering process comprises utilizing the APR-DRG values to identify cases in a specified data set (e.g., system-wide cases) used to evaluate a physician (e.g., Cardiologist A). In this case, the APR-DRG values for Cardiologist A's patients are: 180, 120, and 115. Thus, a computer system implementing one embodiment of the invention (e.g., system 304) is operable to select those cases with matching APR-DRG numbers or values from the hospital system data set (e.g., system cases # 1, 2, 4, 6, 7, 9, 10, and 11).

The adjustment process further comprises sorting all system cases by severity level associated therewith and identifying system cases with a severity level (e.g., either 1 or 2) that matches the types of cases Cardiologist A has treated (e.g., system cases # 1, 2, 7, 9 and 10). System 304 can then calculate system-wide performance averages (i.e., peer averages) based on system cases that satisfy the filtering criteria of APR-DRG values 180 (with severity level 1), 120 (with severity levels 1 and 2), and 115 (with severity level 2) (e.g., system cases # 1, 2, 7, 9 and 10, which are marked with a ✓ and shown in bold in TABLE 1 above). System 304 is operable to compare the peer averages, which are calculated based on a composite of cases matching Cardiologist A's cases, with Cardiologist A's averages to determine if he is doing better or worse than his peer and highlight the comparison results accordingly on a display. As describe before, the performance evaluation can be made on cases over a quarter, 1-year, or 2-years. Peer cases may, but need not, be drawn from the same time frame.

In this manner, only cases that match the physician's profile in this measure are used to evaluate performance. In one embodiment, system 304 is operable to convert the performance evaluation results into an average percentage. In addition to APR-DRG and Severity, other adjustments such as Specialty may be used to filter performance data from a data pool or source (e.g., a hospital system). In the above example for Cardiologist A, if Specialty is to be used to further filter the system-wide cases, only cardiology cases in the hospital system would be used to evaluate performance.

In one embodiment, system 304 is adapted to determine the peer average across a state, applying the same adjustment criteria to data obtained from a state-level data source such as THCIC. For example, for each physician case, system 304 can be programmed to select all identical cases (i.e., identical APR-DRG, severity, etc.) from the THCIC data set and perform the same algorithm as described above to calculate the corresponding THCIC peer average.

Figure 4:
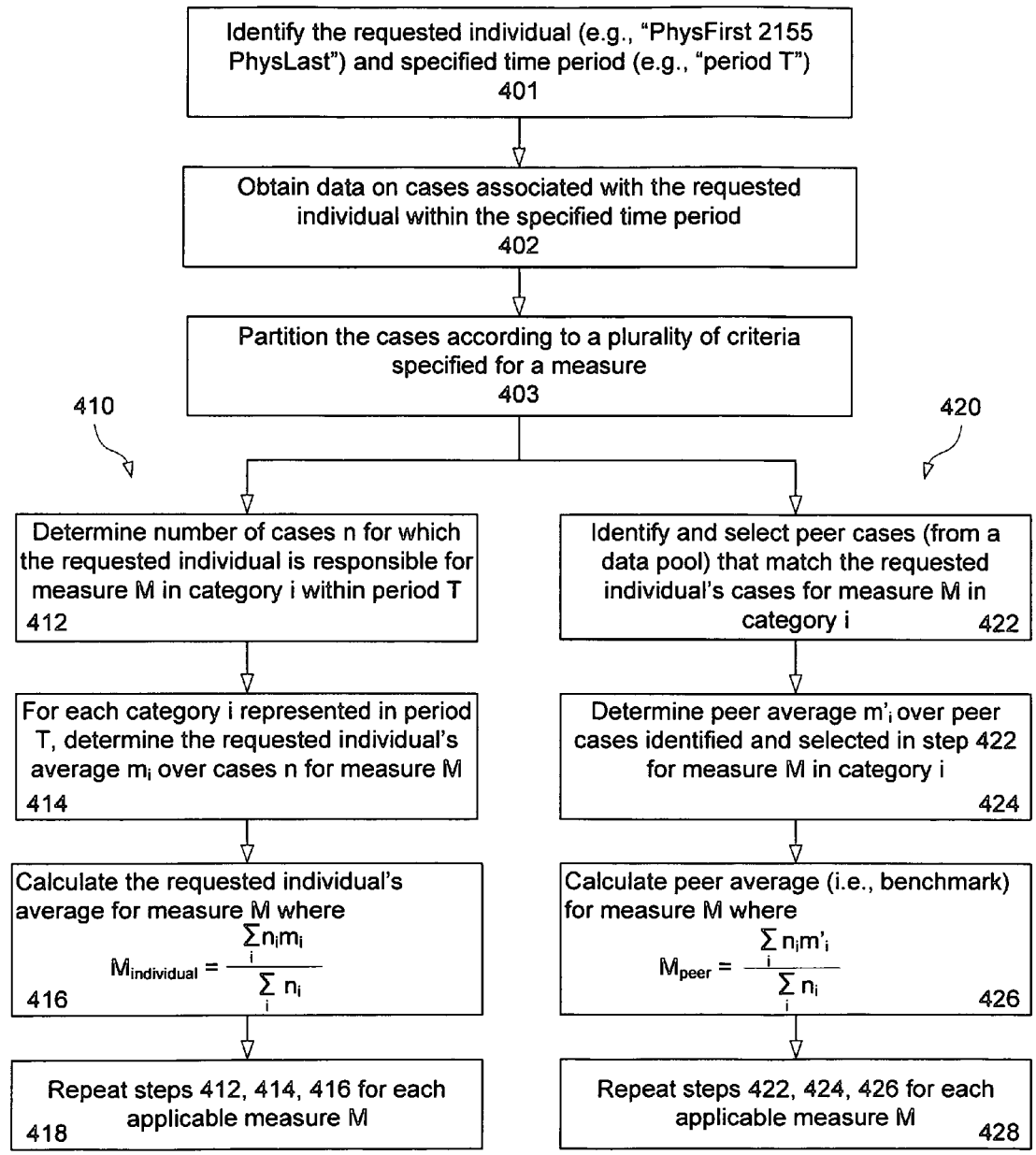
FIG. 4 is a flow diagram illustrating an exemplary peer-profiling process implementing embodiments of the present invention.

FIG. 4 is a flow diagram 400 illustrating another example of the peer-profiling process that can be implemented in various embodiments of the invention. In one embodiment, a computer system (e.g., system 304) can be programmed to interpret a user request (e.g., from client 106) on an individual's performance and extract necessary information (e.g., the individual's identity and performance period, etc.) from the request for analysis at step 401. As describe above, in addition to evaluating individuals, embodiments of the invention can be readily implemented to evaluate an entity or group of individuals. In this example, the individual's identity is represented as "PhyFirst 2155 PhysLast" and the period specified by the user is represented as "period T". One embodiment of the invention can provide peer-profiled performance evaluation on an attending and/or discharging physician. As an example, PhyFirst 2155 PhysLast can be representative of a discharging physician and the peer average results can be calculated based on a composite of cases from multiple discharging physicians.

At step 402, the system is operable to obtain data from a data repository or warehouse (e.g., database 102) on the requested individual's cases within the specified time period. In one embodiment, data obtained from the data warehouse conforms to an industry standard classification system such as APR-DRG. Other implementations are also possible. As one skilled in the art can appreciate, the system may be suitably programmed to adapt to different data classification schemes. In some embodiments, of which step 403 can be optional, partitioned data may also be sorted by measures (i.e., observables such as mortality rates, length of stay (LOS), etc.).

At step 403, the system is operable to partition or classify all cases associated with the requested individual within the specified time period into a plurality of groups according to a plurality of criteria of interest specified for a measure. In one embodiment, specifications on measures are hard-coded into the system. In one embodiment, criteria of interest can cover a variety of medically relevant parameters or factors (e.g., severity level, patient age, patient gender, etc.). The partitioning or segmentation can be done based on a standardized classification scheme as describe above.

In one embodiment, the system may comprise software modules operable to perform a first process 410 comprising steps 412, 414, 416, and 418; and a second process 420 comprising steps 422, 424, 426, and 428, as illustrated in FIG. 4. Process 410 is operable to calculate the requested individual's average for each applicable measure based on the requested individual's cases meeting a particular set of criteria within a specified time period (e.g., the average mortality rate for female patients under the age of 18 within the last quarter). Process 420 is operable to calculate a peer's average for the same applicable measure based on a plurality of cases that meet the same criteria. As described above, these cases may be associated with more than one single physician and may thus form the basis of a composite physician which serves as a virtual peer for performance evaluation purposes. The peer cases may, but do not need to, be selected from the same time period as the evaluation period for the particular physician. In one embodiment, peer data may be sampled or pooled from a period of two years.

More specifically, at step 412, process 410 may operate to determine a number of cases for which the requested individual is responsible within the specified time period (e.g., n cases discharged by PhyFirst 2155 PhysLast with period T). At step 414, for each category i represented in period T, process 410 may operate to determine PhyFirst 2155 PhysLast's average $m_i$ over cases $n_i$ for measure M. At step 416, process 410 may operate to calculate PhyFirst 2155 PhysLast's overall average for measure M (i.e., $M_{individual}$) where $$M_{individual} = \frac{\sum_i n_i m_i}{\sum_i n_i}.$$

Steps 412, 414, and 416 may be repeated at step 418 for each applicable measure hard-coded in the system.

Similarly, at step 422, process 420 may operate to identify and select peer cases that match cases associated with the requested individual for measure M in the same category i. At step 424, process 420 may operate to determine the peer average $m'_i$ over selected peer cases for measure M in the same category i. As described above, these peer cases may be selected from a period of time that is not the same as and could be longer than period T. Furthermore, in calculating the peer average $m'_r$, the number of peer cases may, but does not need to, match the number of cases for which the requested individual is responsible. For matching cases represented in each category i, process 420 may operate to calculate an overall peer average for measure M (i.e, $M_{peer}$) at step 426 where $$M_{peer} = \frac{\sum_i n_i m'_i}{\sum_i n_i}.$$

Steps 422, 424, and 426 may be repeated at step 428 corresponding to step 418.

In this case, $M_{peer}$ may serve as a benchmark representing average peer performance at a certain level (e.g., hospitals, hospital systems, physician groups, state, national, etc.) according to an industry standard such as APR-DRG. As one skilled in the art can appreciate, the size of the data pool may be adjusted depending upon user request (i.e., dynamic) or system specification (i.e., static). Optionally, the underlying system may be suitably adapted to provide an estimate of significance (e.g., by calculating a weighted variance) as well as relevant statistical analyses and/or optimizations. As described below, statistical significance may be utilized to enhance the presentation on a display.

In one embodiment, the system is operable to display the physician average alongside the peer average (i.e., system benchmark). In one embodiment, performance evaluation results can be color-coded (e.g., red if the physician's mortality rate is significantly higher than the peer's mortality rate). In the case of insufficient statistics for comparison (e.g., the physician has fewer than five (5) cases in the time period), the system may be configured to display the result(s) in a neutral color (e.g., grey).

In practice, while an 'average' mortality rate for a particular APR-DRG and Risk of Mortality Level may be defined, not every physician can be expected to always precisely match that rate. Accordingly, the system may be adapted to consider variance in the distribution. In other words, the amount that a physician's score (e.g., $M_{individual}$) deviated from the mean should be judged relative to the amount of variance in that score's distribution over the population of doctors (e.g., at the hospital system level). As an example, if all but 98% of the discharges in a particular APR-DRG/Risk of Mortality class of cases ended without mortality and the physician attained a 50% mortality rate in the same class, the system may be configured to interpret the deviation as being a deviation of interest. If the standard deviation is 30% and the physician's average is well within the standard deviation from the peer average, the system may be configured to accept the deviation.

For this reason, in addition to calculating the peer average for each measure over peer cases in each class or group of data, the system is also operable to determine a peer-based standard per class. In one embodiment, the system can be programmed with suitable software modules implementing known statistical techniques to calculate a peer standard deviation. The peer standard deviation may depend on the peer variance in each class, group, or category of data as well as the physician's actual distribution of cases amongst each class, in analogy to the 'peer average'. Optionally, the system can be programmed to present physician averages against a scale calibrated with the peer average in the center of a graphical display and distance in units of the peer standard deviation on either side of the peer average. This arrangement can facilitate a user (e.g., a performance analyst, an administrator, or the physician himself, etc.) to determine at a glance whether the physician (or any individual or entity under evaluation) has performed significantly better or worse in a category (or class or group, depending upon implementation) compared to his or her peers.

In the above described example, composite peer average and peer standard deviation can be calculated in terms of results at the distinct APR-DRG and Risk of Mortality level. In some embodiments, the manner in which how data is actually broken down or divided into groups (i.e., categorization, classification, partitioning, or segmentation) can depend on the desired or specified measure (i.e., observables). For some calculated values, a comparison of cases with the same APR-DRG and Severity Level may be more appropriate. According to embodiments of the invention, the system can be suitably programmed to segment the data utilizing a variety of possible variables, including, but not limited to, APR-DRG, Severity Level, Risk of Mortality Level, Hospital, Per-Physician, Per-Discharge, etc. These variables can be used in various combinations to segment the data for each measure as appropriate. For some measures, the system can be programmed to provide more than one comparisons. For example, for a set of discharges by a particular physician, each patient's length of stay (LOS) typically depends on what the associated illness is (i.e., APR-DRG) and the illness's severity (i.e., Severity Level). However, the LOS may also have a reasonable dependence on the hospital employing the physician. In this case, the system can provide two different comparisons. That is, the physician's average length of stay can be compared with:

1) peer results based on matching cases (e.g., APR-DRG/Severity combinations) regardless of hospital; and
2) peer results calculated separately for each hospital for which the physician had discharges. In other words, the physician's average length of stay for each hospital is compared to the peer results based on matching cases at that hospital.

As described above, the size of the data pool or system data set may vary depending upon implementation. For some measures, the 'peer average' presented for comparison may be taken from a hospital system's set of discharges over a time period. For some measures, the 'peer average' presented for comparison may be taken from an entire state's body of discharges over a period of similar length (e.g., THCIC results). In the latter case, the same calculations as described above can be carried out over a different set of data. In one embodiment, the actual segmentation used for comparison can be specified for each measure hard-coded in the system.

FIG. 5 shows a screenshot 500 of a user interface implementing one embodiment of the invention. General Hospital 512 may represent an institution or organization (e.g., hospital 112 or hospital system 110 as illustrated in FIG. 1). User 522 represents any person who is authorized, with appropriate user ID and password, to access a computer system 504 implementing one embodiment of the invention. User 522 may be a medical director, chief of service, performance analyst, hospital administrator, manager, or third party investigator. User 522 may be a physician who is requesting his own peer-profiled performance evaluation. As an example, after logging in, user 522 may click on the link "Find a Physician Profile" to search and view profiles. User 522 may enter a physician's last name (e.g., PhysLast) in a search box. System 504 may suitably implement various search techniques known in the art and, in return, display the selected physician's most current profile to user 522.

FIGS. 6-12 show screenshots 600-1200 representative of a comprehensive physician profile, exemplifying embodiments of the invention. In this example, Physician Profile for Phys-First 2155 PhysLast is presented to the requesting user (i.e., user 522) as a Web page having four tabs: Physician, Overview, Quality, and Utilization, as shown in screenshot 600 of FIG. 6. The Physician tab may contain Physician Information (e.g., name, ID, specialty, contact information, etc.), Alerts, and Tasks associated with PhysFirst 2155 PhysLast. These tabs represent different areas of the physician's profile. User 522 may choose to go back and forth between the tabs, looking at different measures in these areas.

Figure 7:
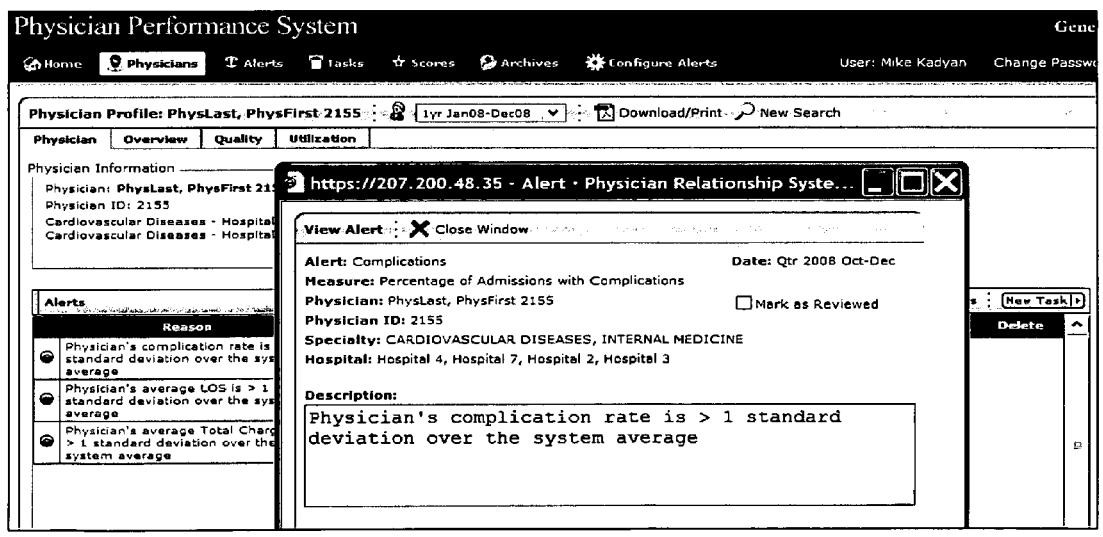

Screenshot 700 of FIG. 7 shows an exemplary View Alert window which allows the authorized user to review an alert associated with PhysFirst 2155 PhysLast, according to one embodiment of the invention. As shown in FIG. 7, such alerts can provide an immediate view of high priority issues that require the user/viewer's attention.

Figure 8:
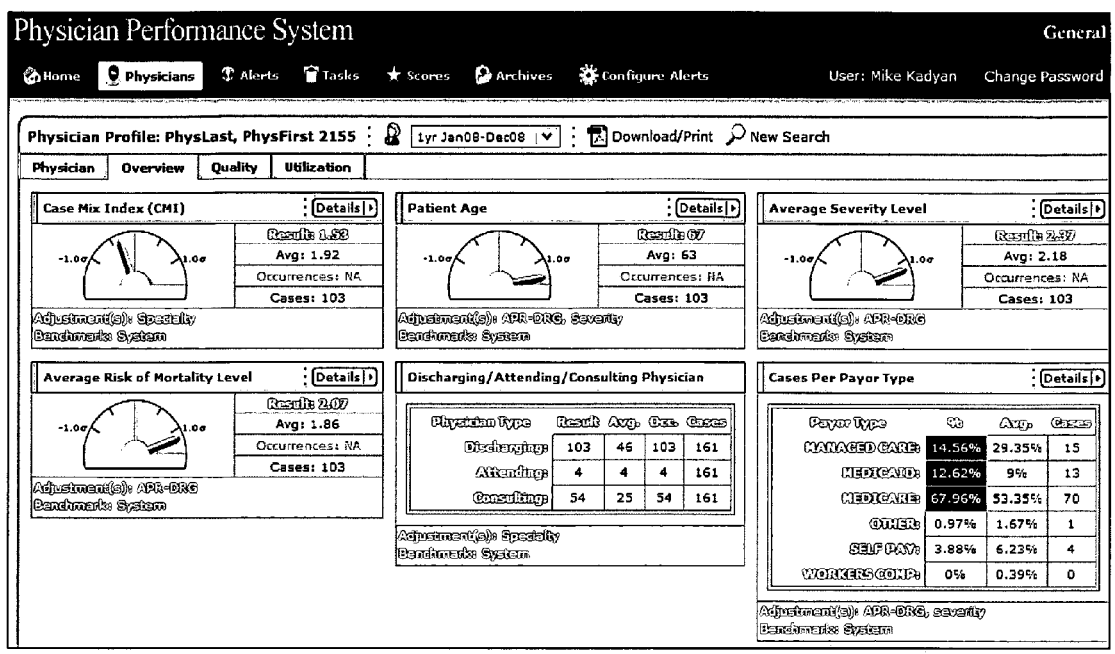

The Overview tab may contain a plurality of windows showing a plurality of performance measures (e.g., Case Mix Index (CMI), Patient Age, Average Severity Level, Average Risk of Mortality Level, etc.), as shown in screenshot 800 of FIG. 8. In this example, each window shows how well Phys-First 2155 PhysLast performs in a particular measure as compared to a benchmark "System" on average. Each benchmark "System" in a measure is representative of a virtual peer of equivalent standing with PhysFirst 2155 PhysLast in that particular measure, as described above with reference to FIGS. 3 and 4. As shown in FIG. 8, each of the plurality of windows may include a "Details" button which can be linked to another Web page or a pop-up window that may provide further details on each measure. The Overview tab may also include types of windows (e.g., Discharging/Attending/Consulting Physician, Cases Per Payor Type, etc.).

Figure 9:
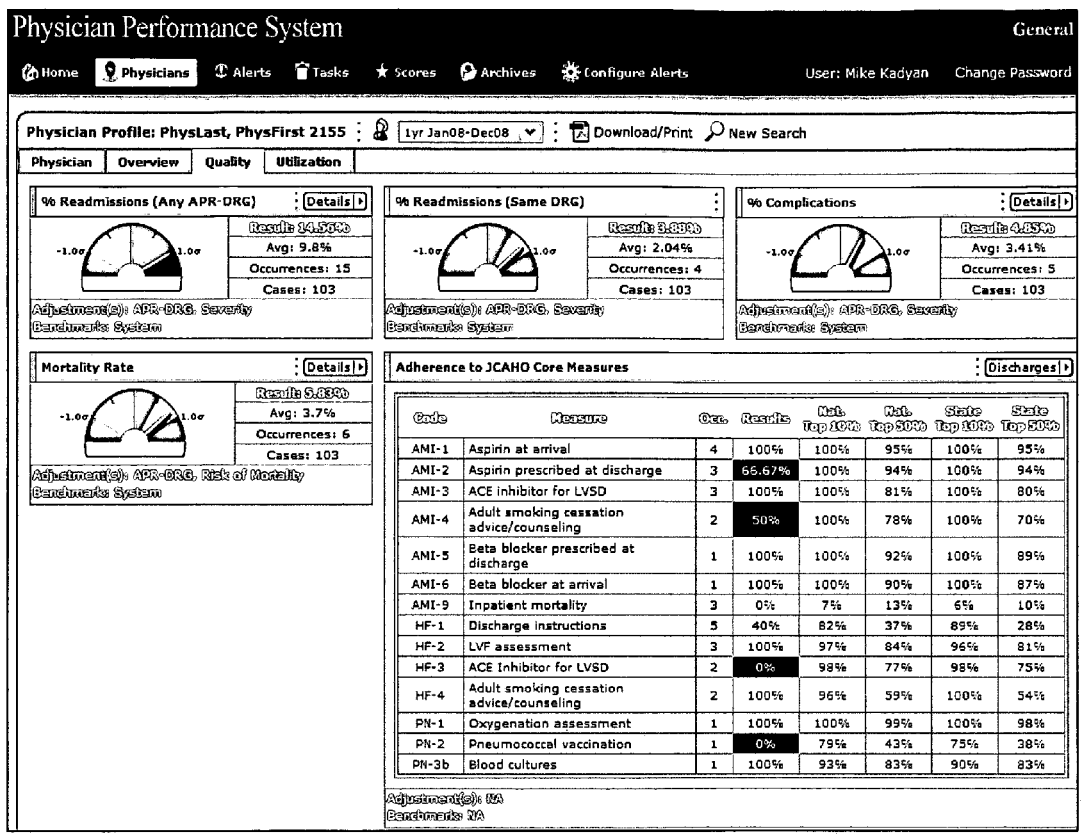

Similarly, as shown in screenshot 900 of FIG. 9, the Quality tab may contain a plurality of windows showing a plurality of quality-related measures (e.g., % Readmissions, % Complications, Mortality Rate, etc.), each comparing PhysFirst 2155 PhysLast with a corresponding benchmark "System". In this example, the Quality tab includes an Adherence to JCAHO Core Measures window in which PhysFirst 2155 PhysLast's adherence to the JCAHO Core Measures is compared with his/her peers at various national- and state-levels. As in FIG. 8, each of the plurality of windows in FIG. 9 may include a "Details" button which is linked to another Web page or pop-up window that may provide further details on each measure.

Figure 10A:
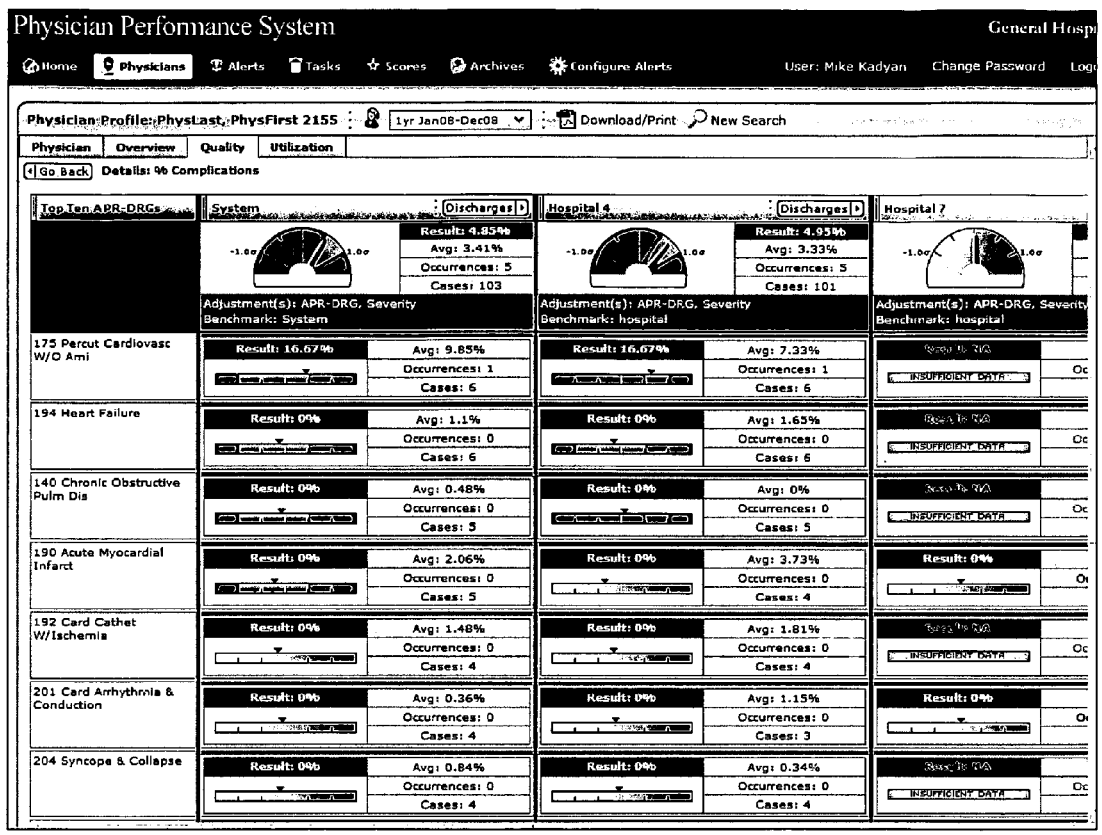
Figure 10B:
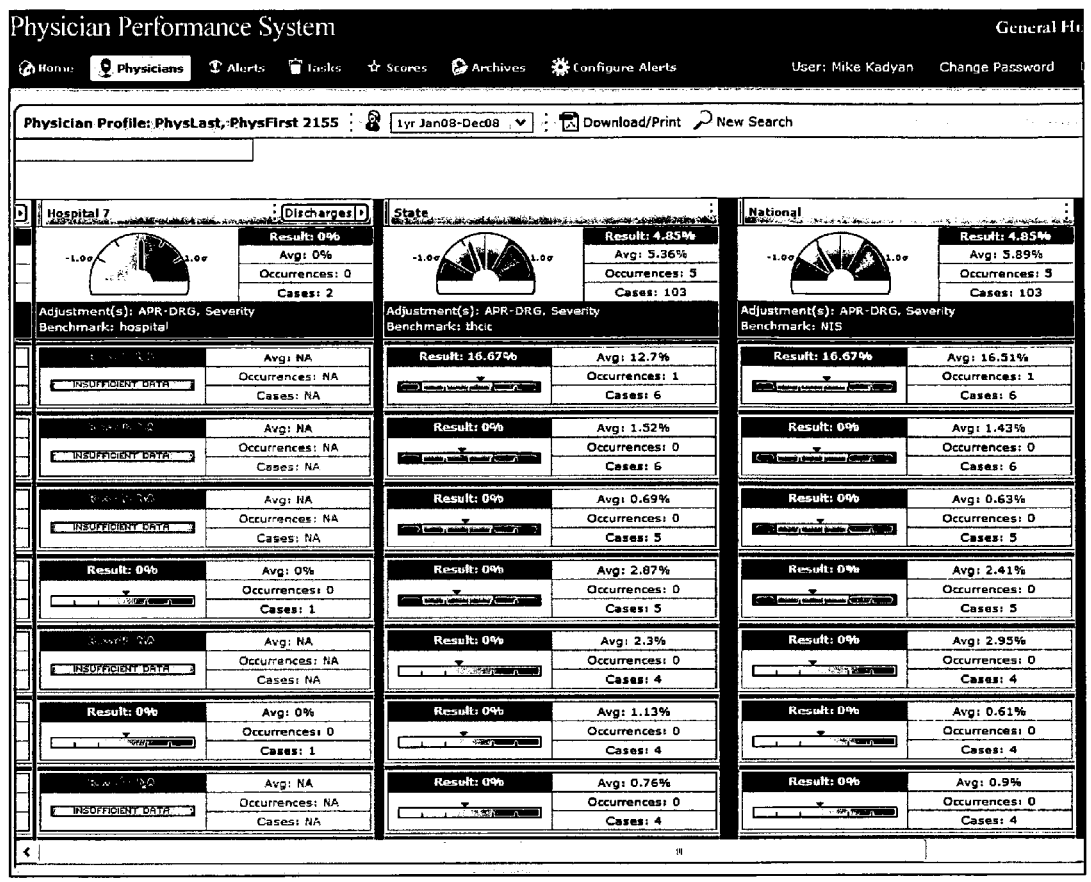

As an example, screenshots 1000a and 1000b of FIGS. 10A and 10B show details on the percent of complications associated with PhysFirst 2155 PhysLast after the Details button in the % Complications window has been selected. As shown in FIGS. 10A and 10B, embodiments of the invention can enable PhysFirst 2155 PhysLast to be compared with different virtual peers (i.e., benchmarks) in different APR-DRG measures at various levels (e.g., hospital system-wide level (System), facility level (Hospital 4, Hospital 7), state level (THCIC), national level (NIS), etc.).

Figure 11:
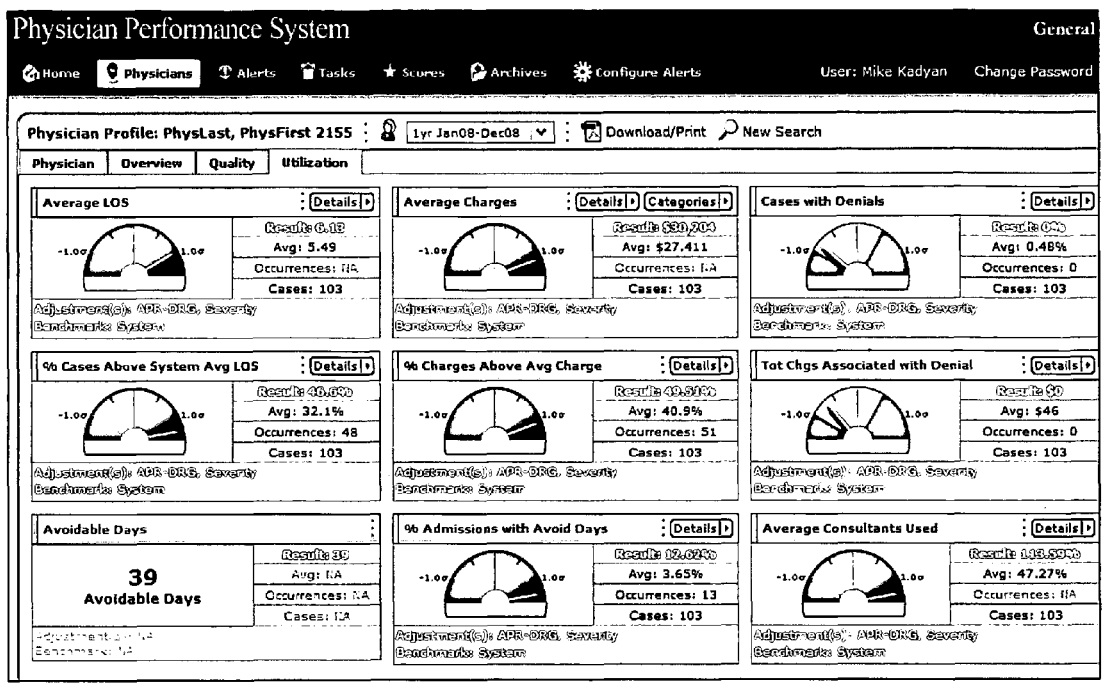

Similarly, as shown in screenshot 1100 of FIG. 11, the Utilization tab may contain a plurality of windows showing a plurality of utilization-related measures (e.g., Average (Avg) Length of Stay (LOS), Average Charges, Cases with Denials, % Cases Above System Avg LOS, % Charges Above Avg Charge, Total (Tot) Charges (Chgs) Associated with Denial, Avoidable Days, % Admissions with Avoidable (Avoid) Days, and Average Consultants Used, etc.). As in FIGS. 8 and 9, each of the plurality of windows in FIG. 11 may include a "Details" button which is linked to another Web page or pop-up window that may provide further details on each measure. Other links may be possible (e.g., "Categories" in the Average Charges window).

Figure 12:
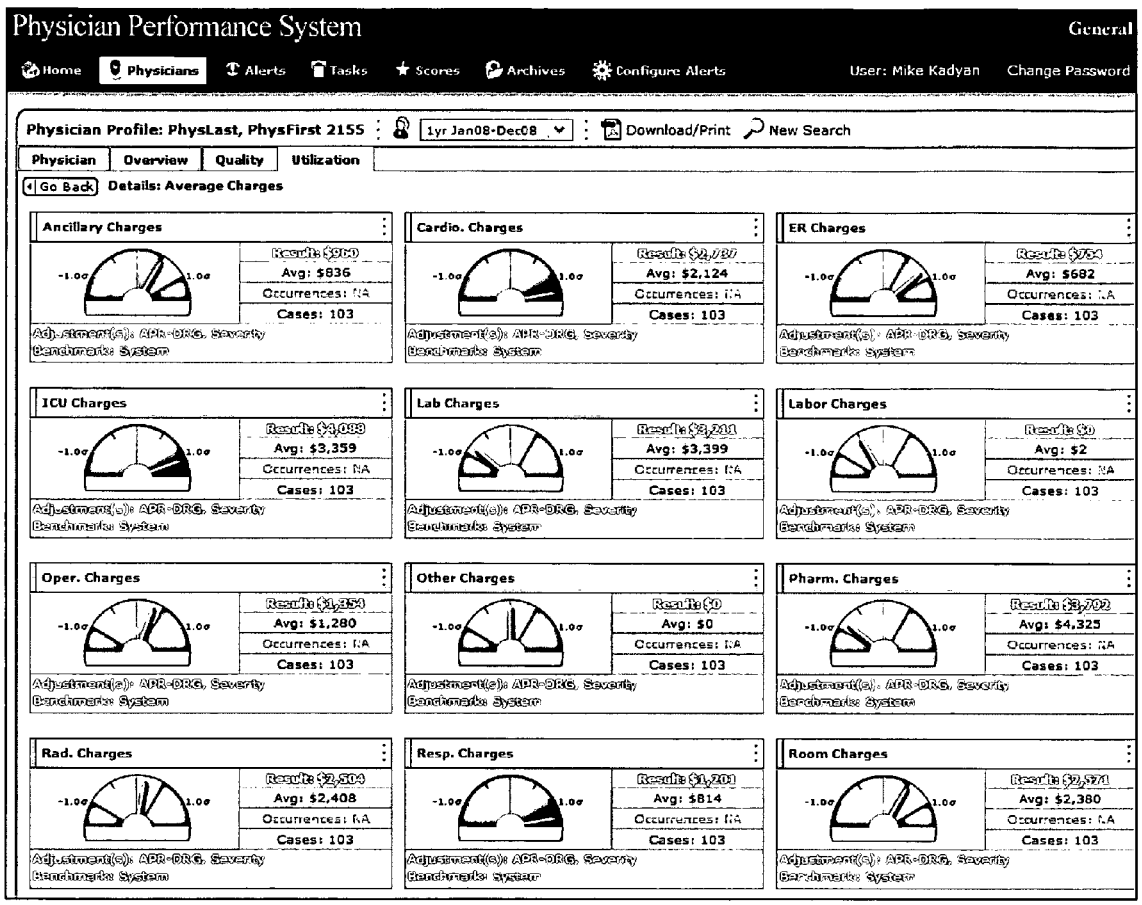

As an example, screenshot 1200 of FIG. 12 shows details on average charges by PhysFirst 2155 PhysLast after the Details button in the Average Charges window has been selected. As shown in FIG. 12, embodiments of the invention can enable PhysFirst 2155 PhysLast to be compared with different virtual peers in different charge categories.

In all cases described above, adjustment can be made according to the diagnoses of individual cases as well as the severity level (i.e., level of sickness and/or mortality) of individual patients so that PhysFirst 2155 PhysLast's performance can be accurately evaluated (i.e., benchmarked) against his/her peer. Since benchmarks can be computed to tailor different measures in different categories with respect to the individual who is being evaluated, benchmarks according to embodiments of the invention can differ from category to category. In addition, benchmarks according to embodiments of the invention can differ from person to person.

In one embodiment, system 504 highlights potential problems or issues in red, allowing user 522 to be quickly drawn to certain measures. For example, PhysFirst 2155 PhysLast may have a mortality measure displayed in red. User 522 can see how PhysFirst 2155 PhysLast compare to his peers in the same specialty (average, min and max) as well as the number of encounters used to calculate the results of the particular measure. User 522 may also learn how PhysFirst 2155 PhysLast compares to state or national benchmarks. In addition, system 504 may provide a statistical confidence percentage level on whether the data is statistically significant. Once user 522 has completed his review, he can proceed to obtain a printed copy of PhysFirst 2155 PhysLast's profile and/or the detailed data associated therewith and log off from system 504.

Although the present invention has been described and illustrated in detail, it should be understood that the embodiments and drawings are not meant to be limiting and should be regarded in an illustrative rather than a restrictive sense. As one of ordinary skill in the art can appreciate, various modifications and changes can be made to the embodiments and drawings disclosed herein without departing from the scope of the present invention. In addition, many alternatives to the examples disclosed herein are possible. All such modifications and alternatives are intended to be included within the scope of present invention. Accordingly, the scope of the invention should be determined by the following claims and their legal equivalents.

The invention claimed is:

1. A method for peer-profiling performance of an entity, comprising:

at a server computer:
in response to a request from a client computer communicatively coupled to the server computer, generating a performance profile of said entity, wherein said entity is representative of one or more individuals, wherein said performance profile comprises a plurality of measures, wherein each applicable measure of said plurality comprises an entity average determined based on a group of cases that meet a set of criteria specific to said applicable measure, wherein said entity is responsible for said group of cases, and wherein if a case for which said entity is responsible does not meet said set of criteria specific to said applicable measure, it is not included in said group of cases;

constructing a virtual peer having an equivalent performance profile with respect to said applicable measure, wherein said constructing step further comprises selecting, from a plurality of peer cases, a composite of cases that also meet said set of criteria specific to said applicable measure, wherein if a peer case does not meet said set of criteria specific to said applicable measure, it is not included in said composite of cases, wherein said group of cases is a subset of a plurality of cases for which said entity is responsible, wherein said composite of cases is a subset of said plurality of peer cases for which two or more peers of said entity are responsible, and wherein both subsets meet said set of criteria specific to said applicable measure, effectuating a meaningful comparison between said entity and said peers of said entity, wherein said equivalent performance profile for said virtual peer comprises a peer average determined based on said composite of cases, and wherein said peer average is specific with respect to said applicable measure;

comparing said performance profile of said entity with said equivalent performance profile of said virtual peer, including:
determining a distribution ratio of said group of cases for which said entity is responsible with regard to said plurality of measures; and
configuring said composite of cases over said distribution ratio; and
returning results to said client computer.

2. The method of claim 1, wherein said entity is responsible for said group of cases within a specified time period.

3. The method of claim 2, wherein said composite of cases is selected to match said group of cases over said specified time period.

4. The method of claim 3, wherein the step of determining an entity average further comprises:
calculating an average value m for said group of cases for said applicable measure; and
calculating $M_{individual}$, where $M_{individual}$ is representative of said entity average, where $$M_{individual} = \frac{\sum_i n_i m_i}{\sum_i n_i} \text{ and where}$$

i is representative of said group and n is representative of a number of cases that meet said set of criteria within said specified time period; and
wherein the step of determining a peer average further comprises:
calculating an average value m' for said composite of cases for said applicable measure; and
calculating $M_{peer}$ where $M_{peer}$ is representative of said peer average and where $$M_{peer} = \frac{\sum_i n_i m'_i}{\sum_i n_i}.$$

5. The method of claim 1, wherein said plurality of peer cases is from a data source associated with a hospital, a hospital system, a state agency, a national agency, an international agency, or an independent agency.

6. The method of claim 1, wherein said individuals are healthcare or medical professionals, including physicians, doctors, and nurse practitioners.

7. The method of claim 1, wherein the step of generating a performance profile of said entity comprises obtaining data on a plurality of cases for which said entity is responsible within a specified time period at an organization, wherein said plurality of cases are classifiable into a plurality of groups according to an industry standard.

8. The method of claim 7, further comprising segmenting said plurality of cases according to All Patient Refined Diagnosis Related Groups (APR-DRG) classification, All Patient DRG classification, or All Patient Severity DRG classification.

9. The method of claim 1, further comprising presenting said results to a user at said client computer, wherein said results include said performance profile of said entity as compared to said equivalent performance profile of said virtual peer in a plurality of classes for said plurality of measures at a plurality of levels.

10. A computer program product comprising at least one non-transitory computer readable medium storing program instructions translatable by at least one processor to perform:
generating, at a server computer, a performance profile of said entity, wherein said entity is representative of one or more individuals, wherein said performance profile comprises a plurality of measures, wherein each applicable measure of said plurality comprises an entity average determined based on a group of cases that meet a set of criteria specific to said applicable measure, and wherein said entity is responsible for said group of cases, and wherein if a case for which said entity is responsible does not meet said set of criteria specific to said applicable measure, it is not included in said group of cases;
constructing a virtual peer having an equivalent performance profile with respect to said applicable measure, wherein said constructing step further comprises selecting, from a plurality of peer cases, a composite of cases that also meet said set of criteria specific to said applicable measure, wherein if a peer case does not meet said set of criteria specific to said applicable measure, it is not included in said composite of cases, wherein said group of cases is a subset of a plurality of cases for which said entity is responsible, wherein said composite of cases is a subset of said plurality of peer cases for which two or more peers of said entity are responsible, and wherein both subsets meet said set of criteria specific to said applicable measure, effectuating a meaningful comparison between said entity and said peers of said entity, wherein said equivalent performance profile for said virtual peer comprises a peer average determined based on said composite of cases, and wherein said peer average is specific with respect to said applicable measure; and
comparing said performance profile of said entity with said equivalent performance profile of said virtual peer, including:
determining a distribution ratio of said group of cases for which said entity is responsible with regard to said plurality of measures; and
configuring said composite of cases over said distribution ratio.

11. The computer program product of claim 10, wherein the non-transitory computer readable medium further comprises instructions translatable by the at least one processor to perform:
obtaining data on a plurality of cases for which said entity is responsible within a specified time period at an organization; and
classifying said plurality of cases into a plurality of groups according to an industry standard.

12. The computer program product of claim 11, wherein said industry standard is representative of All Patient Refined Diagnosis Related Groups (APR-DRG) classification, All Patient DRG classification, or All Patient Severity DRG classification.

13. The computer program product of claim 10, wherein the non-transitory computer readable medium further comprises instructions translatable by the at least one processor to perform:
presenting results to a user at a client computer coupled to said server computer, wherein said results include said performance profile of said entity as compared to said equivalent performance profile of said virtual peer in a plurality of classes for said plurality of measures at a plurality of levels.

14. A computer system for peer-profiling performance of an entity, comprising:
a server configured to receive user requests over a network, wherein, in response to a query on said entity, said server is operable to:
generate a performance profile of said entity, wherein said entity is representative of one or more individuals, wherein said performance profile comprises a plurality of measures, wherein each applicable measure of said plurality comprises an entity average determined based on a group of cases that meet a set of criteria specific to said applicable measure, and wherein said entity is responsible for said group of cases, and wherein if a case for which said entity is responsible does not meet said set of criteria specific to said applicable measure, it is not included in said group of cases;

construct a virtual peer having an equivalent performance profile with respect to said applicable measure, wherein said constructing step further comprises selecting, from a plurality of peer cases, a composite of cases that also meet said set of criteria specific to said applicable measure, wherein if a peer case does not meet said set of criteria specific to said applicable measure, it is not included in said composite of cases, wherein said group of cases is a subset of a plurality of cases for which said entity is responsible, wherein said composite of cases is a subset of said plurality of peer cases for which two or more peers of said entity are responsible, and wherein both subsets meet said set of criteria specific to said applicable measure, effectuating a meaningful comparison between said entity and said peers of said entity, wherein said equivalent performance profile for said virtual peer comprises a peer average determined based on said composite of cases, and wherein said peer average is specific with respect to said applicable measure; and compare said performance profile of said entity with said equivalent performance profile of said virtual peer, including:
  determining a distribution ratio of said group of cases for which said entity is responsible with regard to said plurality of measures; and
  configuring said composite of cases over said distribution ratio.

15. The computer system of claim 14, further comprising:
a data repository communicatively coupled to said server, wherein said server is further operable to access said data repository and obtain data on a plurality of cases for which said entity is responsible within a specified time period at an organization.

16. The computer system of claim 15, wherein said server is further operable to classify said plurality of cases into a plurality of groups according to an industry standard.

17. The computer system of claim 14, further comprising:
a client communicatively coupled to said server via said network, wherein said server is further operable to present results over said network to a user at said client, wherein said results include said performance profile of said entity as compared to said equivalent performance profile of said virtual peer in a plurality of classes for said plurality of measures at a plurality of levels.

* * * * *